（12） United States Patent
Tomita

(10) Patent No.: US 6,286,960 B1
(45) Date of Patent: Sep. 11, 2001

(54) OPHTHALMIC APPARATUS

(75) Inventor: Seiki Tomita, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/536,471

(22) Filed: Mar. 28, 2000

(30) Foreign Application Priority Data

Mar. 30, 1999 (JP) .................................................. 11-088598

(51) Int. Cl.⁷ .............................................................. A61B 3/00
(52) U.S. Cl. .................................................................. 351/245
(58) Field of Search ........................................ 351/208, 244, 351/245; 248/118; 297/391, 392; 359/857; 606/4, 5, 6

(56) References Cited

U.S. PATENT DOCUMENTS 4,128,317 * 12/1978 LeCover ............................... 351/245
5,900,997 * 5/1999 Shspiro ................................. 359/857

FOREIGN PATENT DOCUMENTS 6-142130    5/1994   (JP) .
8-299272   11/1996   (JP) .
11-309170  11/1999   (JP) .

* cited by examiner

Primary Examiner—George Manuel
(74) Attorney, Agent, or Firm—Finnegan, Henderson, Farabow, Garrett & Dunner, L.L.P.

(57) ABSTRACT

An ophthalmic apparatus includes a base board 5, a main unit 1 detachably mounted on the base board, and a head support unit 10 fixed on the base board. This head support unit 10 includes a pair of columns 14R, 14L foldable to the base board 5. With the main unit 1 dismounted from the base board 5, the head support unit 10 is folded until it becomes parallel with the base board 5. The apparatus can thus be housed in a small transportation case when transported. 3

16 Claims, 6 Drawing Sheets

OPHTHALMIC APPARATUS

BACKGROUND OF THE INVENTION

1. Field of the Invention

The present invention relates to an ophthalmic apparatus for performing observations, measurements, and laser treatments with respect to a patient's eye, the apparatus being provided with a head support unit for supporting the head of the patient to hold the patient's eye in position.

2. Description of Related Art

In some instances, ophthalmic apparatus for performing observations, measurements, and laser treatments with respect to a patient's eye are transported from a location to another as required. For example, when a single ophthalmic laser treatment apparatus used for treating an affected part of a patient's eye by irradiating the eye with a treatment laser beam is shared among plural hospitals or clinics, this laser treatment apparatus is needed transporting from one of the hospitals or clinics to another. For enabling transportation, the apparatus is housed in a transportation case which protects the apparatus and provides ease of transportation thereof.

The ophthalmic laser treatment apparatus generally includes a slit lamp used for observation of a patient's eye and a main unit including a laser irradiation optical system. Those slit lamp and main unit are movably mounted on a base board. On this base board, also fixed is a head support unit for fixedly supporting the head of a patient. In association therewith, a transportation case for packing the apparatus as an integral unit is needed increasing in size. This causes deterioration in transportability of the case packing the apparatus therein. Also, if the case is large in weight, even the transportation thereof would not be easy.

SUMMARY OF THE INVENTION

The present invention has been made in view of the above circumstances and has an object to overcome the above problems and to provide an ophthalmic apparatus capable of being packed in a transportation case of a smaller size as compared with a conventional case for ophthalmic apparatus of an integral unit type, thereby providing improved transportability.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an ophthalmic apparatus including: a base board; a main unit detachably mounted on the base board; and a head support unit fixed on the base board, the unit being at least foldable to or detachable from the base board.

According to the present invention, the apparatus can be packed or housed in a compact form in a smaller transportation case as compared with a conventional case. This can improve transportability of the apparatus.

According to another aspect of the present invention, there is provided an ophthalmic apparatus including: a base board; a main unit; a head support unit fixed on the base board; means for enabling mounting and dismounting of the main unit with respect to the base board; and means for changing a fixing state of the head support unit with respect to the base board.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1A:
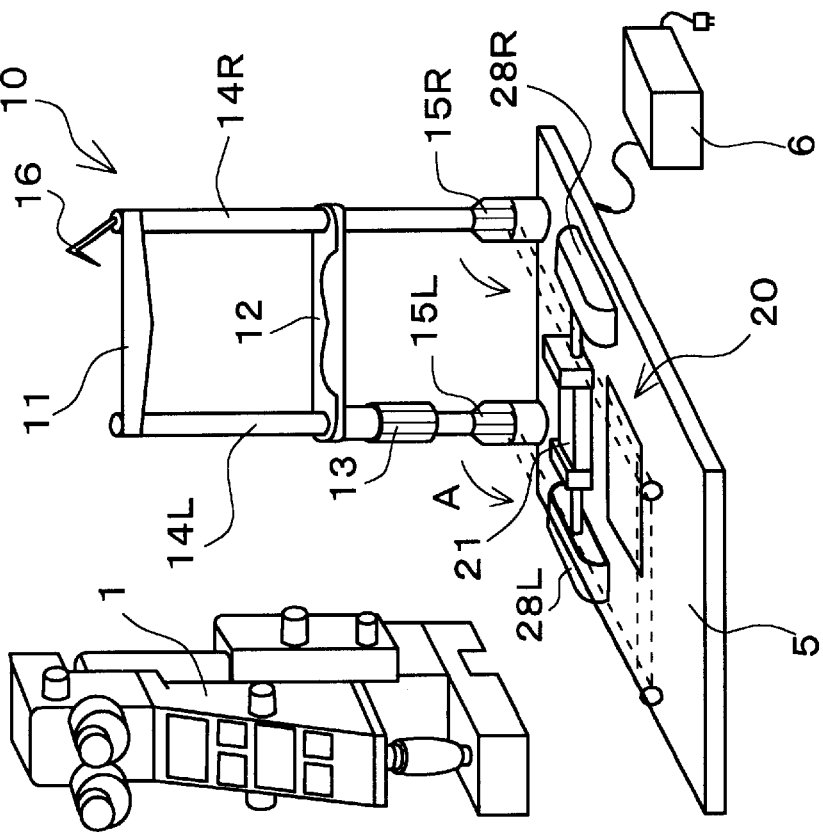
FIG. 1A is a perspective view of an ophthalmic laser treatment apparatus in an embodiment according to the present invention.
Figure 1B:
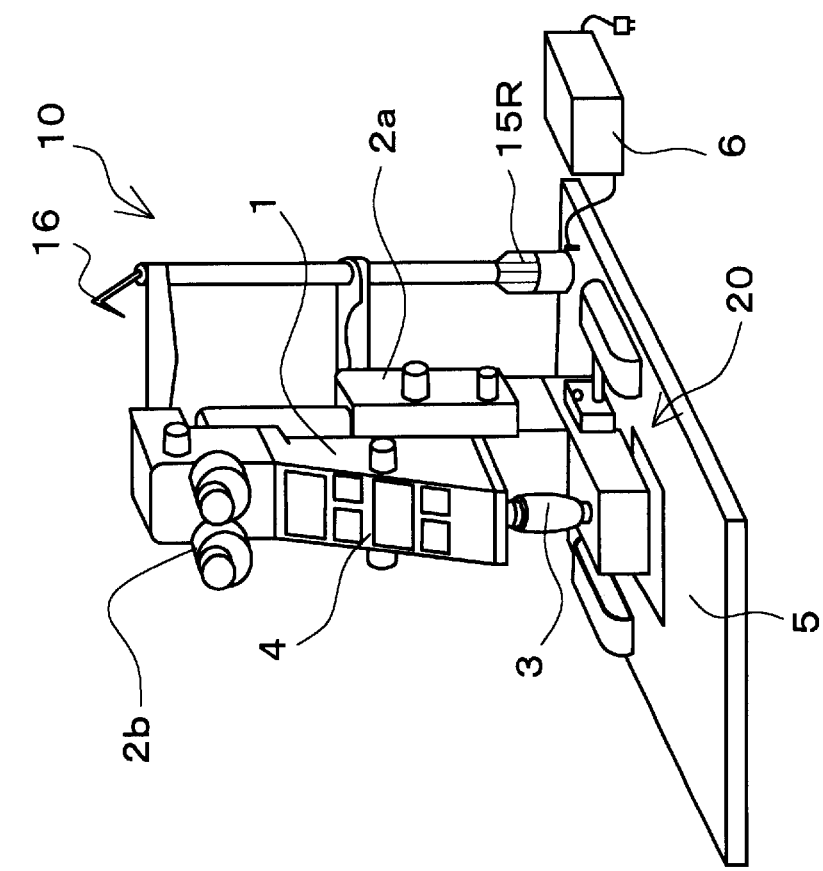
FIG. 1B is a perspective view of the apparatus of FIG. 1A in another state in which a main unit is dismounted from a base board.
Figure 2:
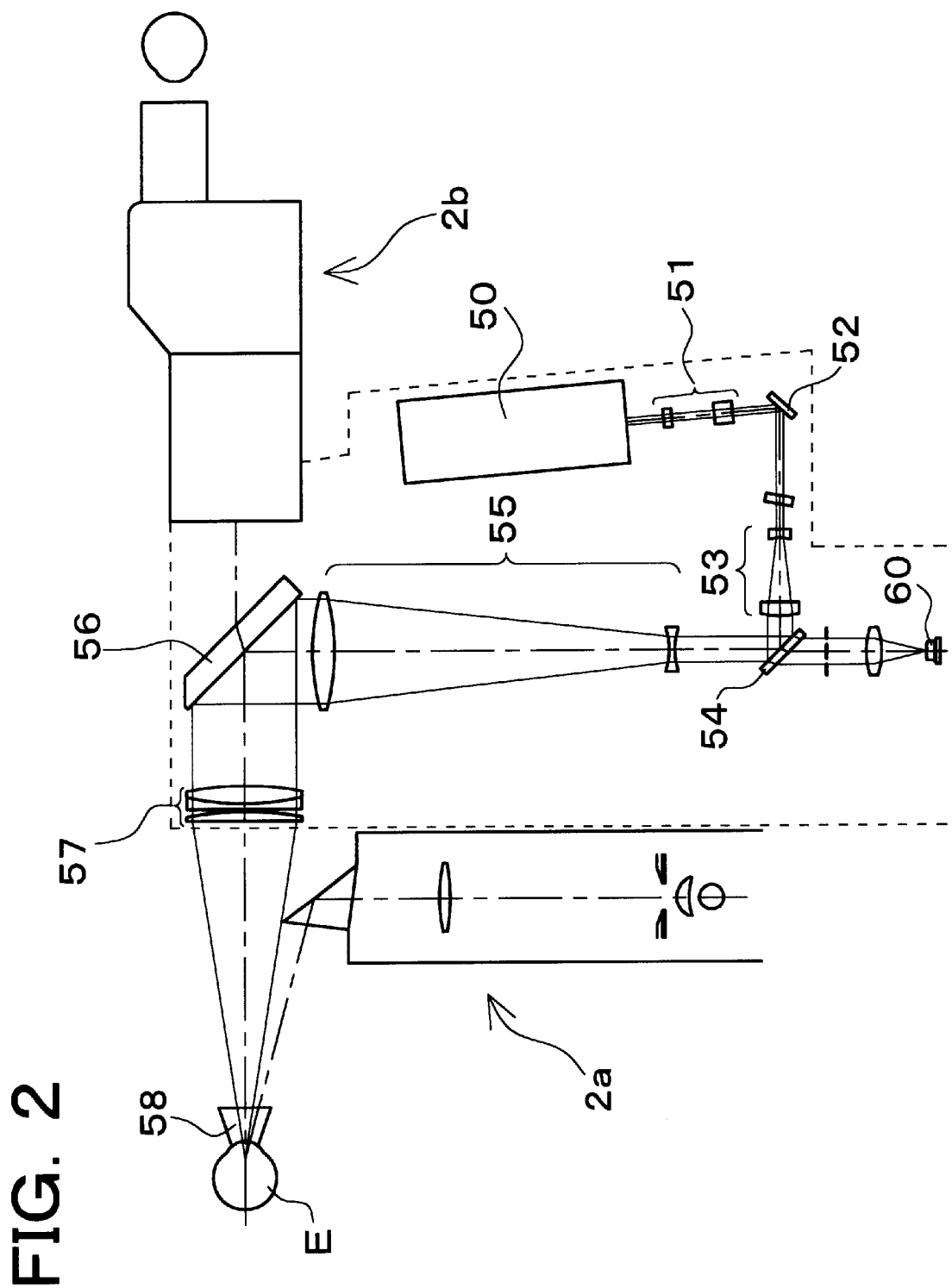
FIG. 2 is a schematic diagram of optical systems of the ophthalmic apparatus in the present embodiment.

A detailed description of one preferred embodiment of an ophthalmic apparatus embodying the present invention will now be given referring to the accompanying drawings. FIG. 1A is a perspective view of the ophthalmic apparatus in the present embodiment according to the present invention. FIG. 1B is a perspective view of the apparatus in a state where a main unit is dismounted from a base board of the apparatus. FIG. 2 is a schematic diagram of optical systems of the apparatus.

Reference numeral 1 denotes a main unit that includes therein a slit lamp illuminating section 2a for illuminating a patient's eye E with slit-light, a slit lamp microscope section 2b through which an operator observes the eye E, a YAG laser source 50 used as a treatment laser source, a semiconductor laser source 60 used as an aiming light source, and light delivery optical system for delivering light beams emitted from the light sources to the eye E.

A treatment laser beam (hereinafter referred to as a treatment beam) emitted from the laser source 50 passes an output power control optical system 51, a mirror 52, and expander lenses 53, and is reflected by a dichroic mirror 54. This dichroic mirror 54 has the property of reflecting a treatment beam, while allowing a visible aiming light beam emitted from the light source 60 to pass therethrough. The treatment beam reflected by the mirror 54 is made coaxial with the aiming beam and passes beam expander lenses 55, thereafter it is reflected by a dichroic mirror 56. This dichroic mirror 56 has the property of reflecting a treatment beam and a part of an aiming beam, while allowing an observation light to pass therethrough. The treatment beam reflected by the dichroic mirror 56 sequentially passes an objective lens 57 and a contact lens 58, and it is projected onto the eye E.

Reference numeral 3 is a joystick that is used for alignment of the main unit 1 with respect to the eye E to be irradiated with a treatment beam by moving the main unit 1 in a right/left and forward/backward directions on the base board 5. A rotating knob is provided on the joystick 3 to perform alignment of the apparatus in an up/down direction. Thus, the main unit 1 can also be moved up and down by manual rotation of the rotating knob. The joystick 3 is also provided at the top portion thereof with a trigger switch (not shown) for starting emission of a treatment beam. Reference numeral 4 is a control panel used for setting various irradiation conditions of a treatment beam and others.

Reference numeral 5 is a base board on which the main unit 1 is detachably mounted and a head support unit 10 mentioned later is foldably mounted. On this base board 5, a movement system 20 is installed for moving the main unit 1 in right/left and forward/backward directions. The main unit 1 can be readily mounted on and dismounted from a movable base block 21 (mentioned later in detail) of the movement system 20. When the unit 1 is dismounted from the base block 21 as shown in FIG. 1B, it can be transported separately from the base board 5.

Reference numeral 6 denotes an adapter for power supply, which can be easily connected to and disconnected from the base board 5. When the adapter 6 is connected to the base board 5 by a power cable not shown, the main unit 1 connected to the base board 5 by a cable not shown is powered from a power source not shown through the base board 5 connected to the adapter 6.

Reference numeral 10 is a head support unit for fixedly supporting the face, or head, of a patient in place with respect to the main unit 1. This unit 10 includes a brow-rest 11 for supporting the forehead of the patient and a chin-rest 12. This chin-rest 12 is adjustable in an up/down direction by the use of a knob 13 according to the height of the patient's head. Reference numerals 14R, 14L are columns for supporting therebetween the brow-rest 11 and the chin-rest 12. Fixing knobs 15R, 15L are slidably attached to lower portions of those columns 14R, 14L respectively. By means of the fixing knobs 15R, 15L, the columns 14R, 14L are vertically fixed on the base board 5. When the knobs 15R, 15L are turned to come loose, the columns 14R, 14L are allowed to fold in a direction of an arrow A in FIG. 1B by bringing each tip end of the columns close to the base board 5 until the entire head support unit 10 becomes substantially parallel with the base board 5. This folding mechanism will be mentioned later in detail.

Reference numeral 16 denotes a fixation lamp for making a patient to fix his eye on the lighted lamp. The lamp 16 is powered from the main unit 1 by a power cable not shown extending through the inside of the column 14R to connect between the lamp 16 and the main unit 1.

Figure 3:
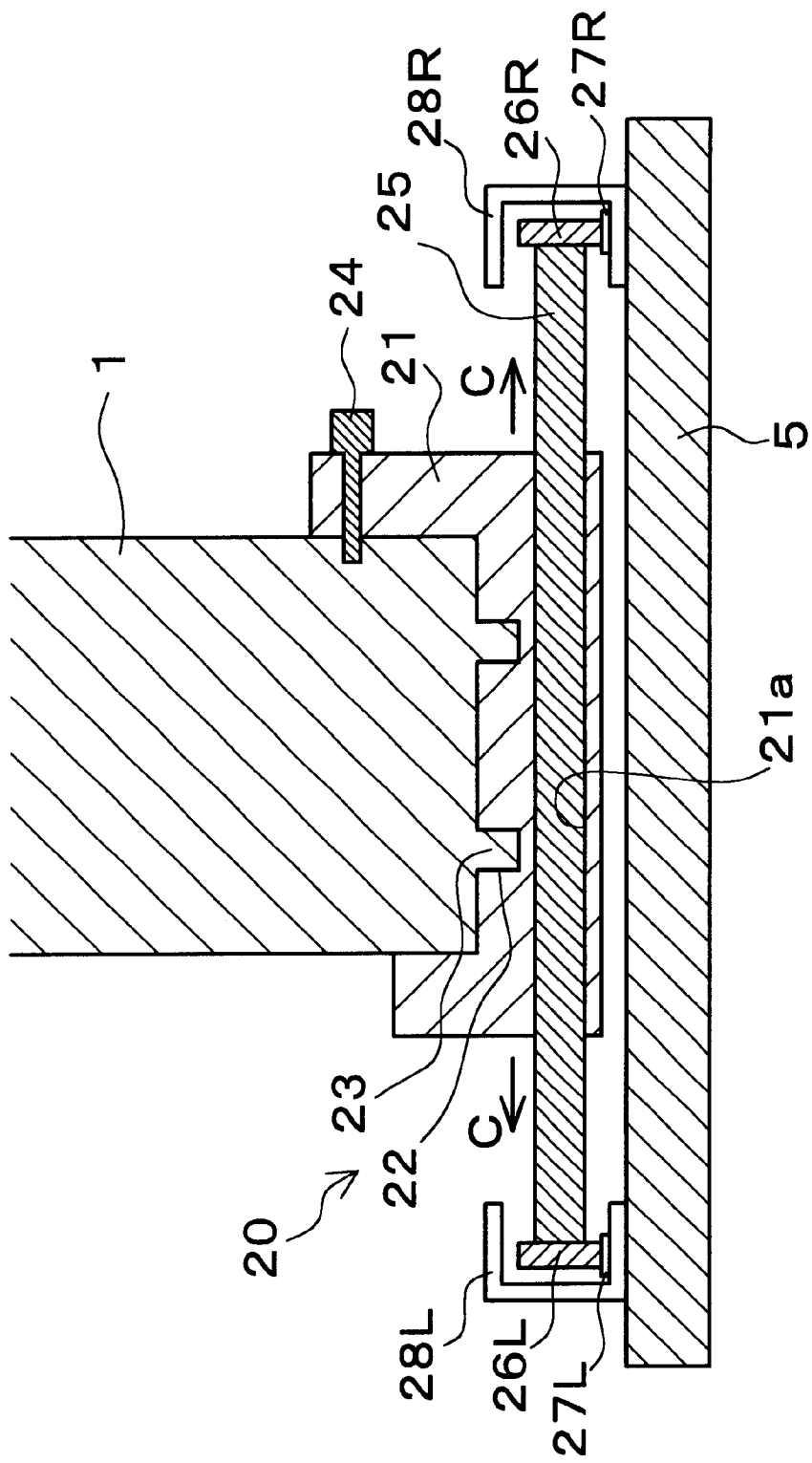
FIG. 3 is a schematic side sectional partial view of a mounting structure of the main unit on a movable base block of a movement system in the present embodiment.

FIG. 3 is a schematic sectional view of a part of the main unit 1 mounted on the movement system 20. The unit 1 is fixedly mounted on the base block 21 of the movement system 20. Specifically, this base block 21 is provided with two recesses 22 on the upper face which are engaged with two projections 23 formed on the bottom of the main unit 1. The block 21 also has an inner shape conformable to an outer bottom shape of the main unit 1. With the projections 23 engaged with the recesses 22, the main unit 1 can be easily secured to the base block 21 by a screw 24. Loosening the screw 24, the main unit 1 can be readily disassembled from the block 21.

An axle 25 is rotatably inserted in a through hole 21a of the base block 21 so that the block 21 may be slid in an axial direction of the axle 25. The sliding of the block 21 and the rotating of the axle 25 are facilitated by means of a bearing not shown. Gears 26R, 26L are attached to both ends of the axle 25 and engaged with a pair of rails 27R, 27L. These rails 27R, 27L are formed with rack teeth and laid on the base board 5 in parallel with each other and in an orthogonal direction to the drawing sheet of FIG. 3. With such the configuration, when force in a forward/backward direction (i.e., a lengthwise direction of the rails 27R, 27L) is exerted on the base block 21, the gears 26R, 26L fixed to the axle 25 are rotated in engagement with the rails 27R, 27L, making it possible to move the base block 21 in the forward/backward direction. Alternatively, when force in a right/left direction (i.e., the axial direction of the axle 25) is exerted on the block 21, the block 21 is slid on the axle 25 in the direction indicated by an arrow C in FIG. 3. Accordingly, the above movement system 20 enables movement of the main unit 1 mounted on the base block 21 in the frontward/backward and right/left directions on the base board 5. It is to be noted that the joystick 3 is provided with a supporting mechanism (not shown) contacting the surface of the base board 5 for horizontally movably supporting the main unit 1 on the base board 5. Reference numerals 28R, 28L are covers that covers the rails 27R, 27L along their entire lengths for protecting the gears 26R, 26L put on the rails 27R, 27L.

Figure 4A:
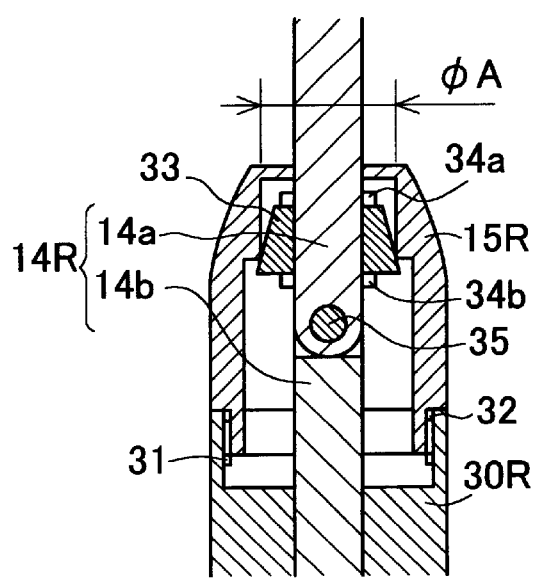
FIG. 4A is a side sectional view of a folding mechanism of a head support unit, showing a state where a knob is screw-engaged with a knob retainer.

FIG. 4A is a schematic sectional view of the folding mechanism of the head support unit 10 viewed from side. Since the folding mechanisms provided to the columns 14R, 14L respectively have the same structure, only the mechanism of the column 14R side is explained below.

The column 14R in the present embodiment includes a first portion 14a for supporting the brow-rest 11 and the chin-rest 12 and a second portion 14b fixed on the base board 5.

Reference numeral 30R is a knob retainer that has an internally threaded portion, or a female screw 31 as illustrated. In association with this configuration, the knob 15R has an externally threaded portion, or a male screw 32, which is engageable with the female screw 31 of the retainer 30R. An engagement member 33 is arranged between the column 14R and the inside of the knob 15R. This engagement member 33 has a truncated cone shape tapered down to a top end of a small diameter and four evenly spaced slits 33a cut by a predetermined deep in the other end (bottom end) of a large diameter. The thus shaped engagement member 33 can be widened or reduced in the diameter of the bottom end.

The engagement member 33 is fixedly attached against movement to the first portion 14a of the column 14R in a predetermined position by means of an upper and lower stoppers 34a, 34b.

Figure 4B:
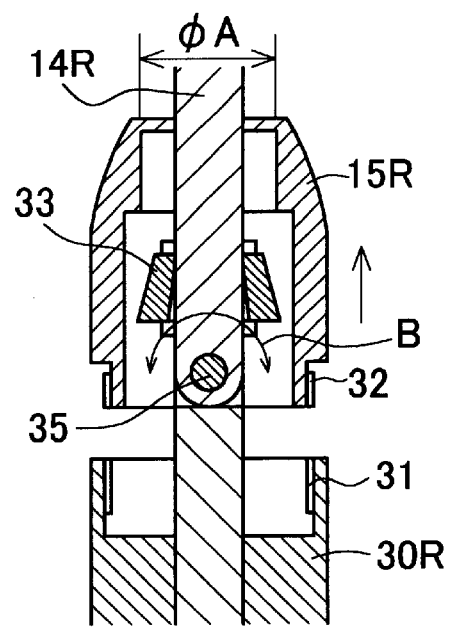
FIG. 4B is a side sectional view of the folding mechanism, showing another state where the knob is disengaged from the knob retainer.
Figure 4C:
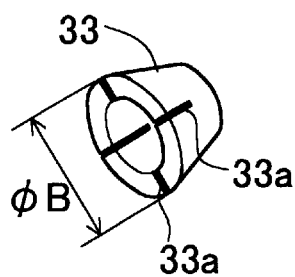
FIG. 4C is a schematic perspective view of an engagement member used in the folding mechanism.

The engagement member 33 is so designed that the outer diameter øB of the bottom end with the slits 33a (see FIG. 4C) is slightly larger than the inner diameter øA of an upper portion of the knob 15R (see FIG. 4B). In the state where the knob 15R is screw-engaged with the retainer 30R as shown in FIG. 4A, a lower end of the inside wall of the upper portion of the knob 15R having the inner diameter øA is in contact with the engagement member 33 at a position slightly above the bottom end with the large diameter (the outer diameter øB) of the engagement member 33. Thus, a larger load than is necessary is prevented from exerting on the engagement member 33. Also, the member 33 is pressed by the inside wall of the upper portion of the knob 15R, reducing the bottom end diameter, and thus coming into close contact with the column 14R. The column 14R is securely held by the knob 15R by means of the engagement member 33 so that the first portion 14a is straight with the second portion 14b, namely, upright on the base board 5.

To the contrary, when the knob 15R is loosened from the retainer 30R as shown in FIG. 4B, the engagement member 33 is not pressed by the inside wall of the knob 15R and the bottom end of the member 33 returns to have an original diameter (øB). Thus, the first column portion 14a is released from the secured state and then can not be fixed vertically on the base board 5.

Figure 4D:
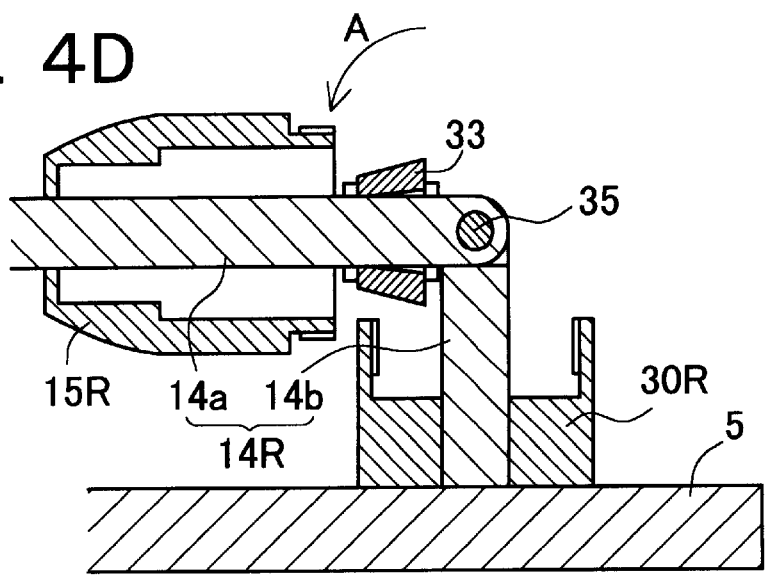
FIG. 4D is a side sectional view of the folding mechanism, showing another state where a first column portion is folded leftward.

Reference numeral 35 is a rotatable shaft serving to fold the first column portion 14a. As mentioned above, when the knob 15R is disengaged from the retainer 30R as shown in FIG. 4B, the first column portion 14a can not be fixedly held vertically. In this state, the shaft 35 becomes rotatable in a direction indicated by a double-headed arrow B in FIG. 4B. The first column portion 14a rotatably connected with the second column portion 14b with the shaft 35 is allowed to fold in a direction indicated by an arrow A in FIG. 4D. As a result, the head support unit 10 can be folded to become substantially parallel with the base board 5.

Next, explanation is made on assembling and disassembling of the above ophthalmic apparatus when it is housed in a transportation case.

At first, the cables for connecting between the adapter 6 and the base board 5 and between the main unit 1 and the board 5 are removed. The screw 24 is loosened to enable dismounting of the main unit 1 from the base block 21. With the screw 24 loose, the main unit 1 is lifted up while disengaging the projections 23 from the recesses 22 of the block 21. Thus, the main unit 1 is dismounted from the base board 5.

Subsequently, folding of the head support unit 10 is performed in the following manner. The knobs 15R, 15L are both loosened to be disengaged from the knob retainers 30R, 30L respectively, and lifted up as shown in FIG. 4B. As a result, the columns 14R, 14L are brought in a foldable state as mentioned above. The columns 14R, 14L are then folded in the direction A in FIGS. 1 and 4D to become substantially parallel with the base board 5.

Figure 5A:
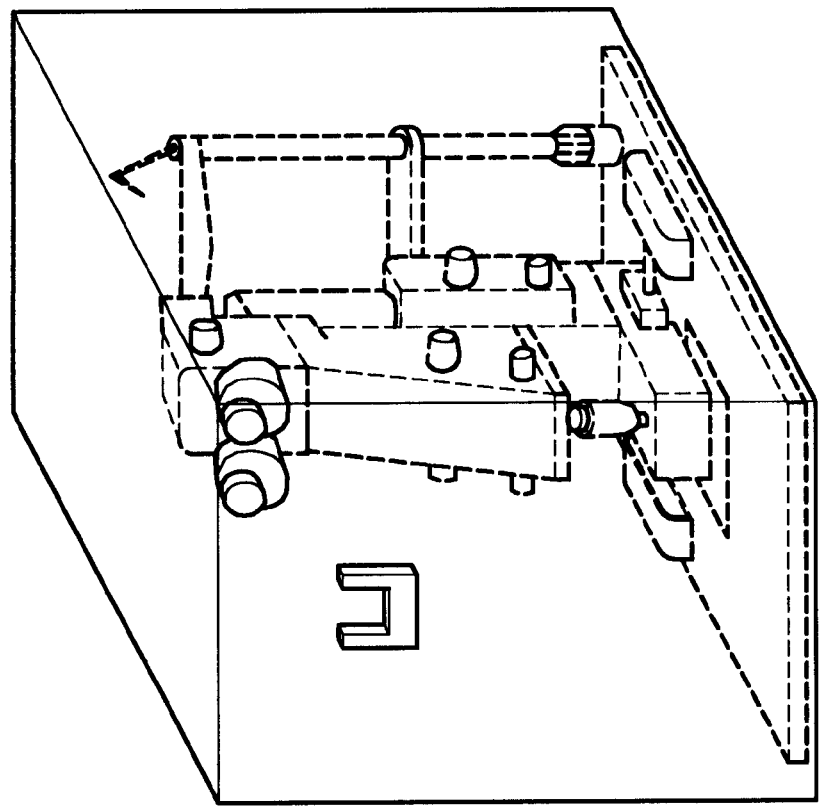
FIG. 5A is a schematic perspective view of the ophthalmic apparatus housed in a transportation case according to the present invention.

As mentioned above, the main unit 1 is disassembled from the base board 5. After disassembling of the main unit 1, the head support unit 10 is folded to become substantially parallel with the baseboard 5. This makes it possible to arrange the base board 5 and the head support unit 10 in a compact state. The main unit 1 separated from the base board 5, the base board 5 and the folded head support unit 10 can be efficiently housed together in a transportation case 100 as shown in FIG. 5A, which is smaller than a conventional case (see FIG. 5B), thus reducing a wasted space. If the board 5 and the main unit 1 are large in weight, individual cases may be prepared for transporting the board 5 and the main unit 1 separately. This can further improve transportability. It is to be noted that small parts and elements such as the adapter 6 may be put in an empty space within the case, reducing a wasted space.

Figure 5B:
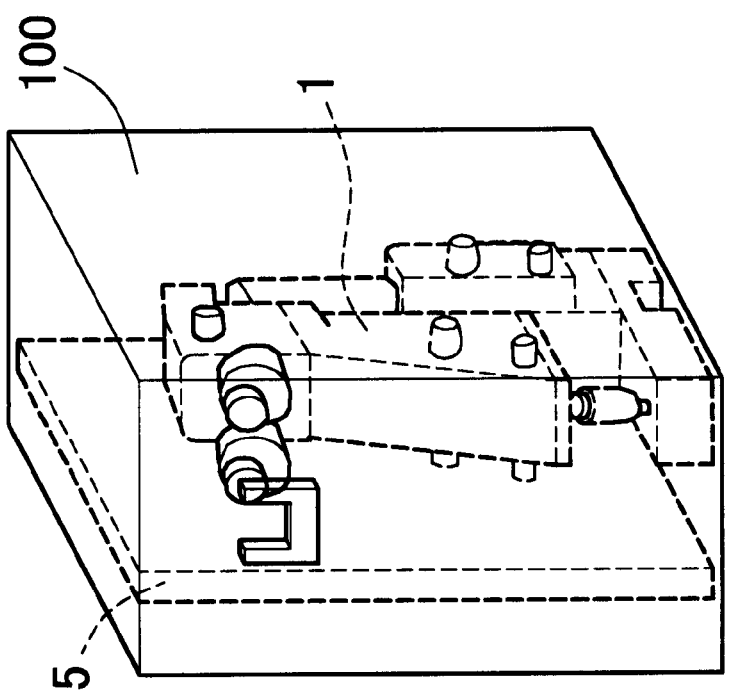
FIG. 5B is a schematic perspective view of a conventional ophthalmic apparatus housed in a transportation case.

To the contrary, if the apparatus is attempted to transport with the main unit 1 and the head support unit 10 fixed on the board 5, it needs an extremely larger case to house the entire apparatus, as shown in FIG. 5B. This deteriorates transportability.

Included among conventional laser treatment apparatus is an apparatus constructed such that only a laser irradiation unit is detachable and transportable for improving transportability. Only the laser irradiation unit detached from a laser treatment apparatus is housed in a corresponding case and transported to a location where another apparatus is installed. The transported unit is then mounted on a slit lamp of the apparatus installed therein. Such the apparatus with a detachable laser irradiation unit therefore does not needs a large case enough to house the entire apparatus. However, since the laser irradiation unit should be mounted later on the slit lamp, the optical accuracy therebetween tends to become low. Furthermore, there may be cases where some constituent elements of the laser irradiation unit are omitted to reduce the weight of the transportable unit for improvement of transportability thereof, thus causing deterioration in laser performance.

On the other hand, the apparatus according to the present invention can be transported with the units disassembled and housed in a single or plural cases, thereby enabling improvement of transportability of the apparatus without causing the lowering of optical accuracy and the deterioration in laser performance.

Assembly of the unit 1 and the board 5 separately or together transported is simply the reverse of disassembly. Specifically, the base board 5 when taken out of the transportation case is put on a flat place, for example, on a medical table. The folded head support unit 10 is unfolded to become upright on the base board 5. The knobs 15R, 15L are then screw-engaged with the knob retainers 30R, 30L respectively. Thus, the columns 14R, 14L are vertically secured on the board 5. In this state, folding of the columns 14R, 14L is impossible. The main unit 1 is mounted on the base block 21 of the movement system 20 and secured thereto by the screw 24. Thus, the apparatus can be assembled in simple steps.

The present invention may be embodied in other specific forms without departing from the spirit or essential characteristics thereof.

For instance, in the above mentioned embodiment, the folding mechanism is used for changing a fixing state of the head support unit 10 with respect to the board 5, but the present invention is not limited thereto. A disengaging mechanism whereby the head support unit 10 is dismounted from the board 5 may be used.

Figure 6A:
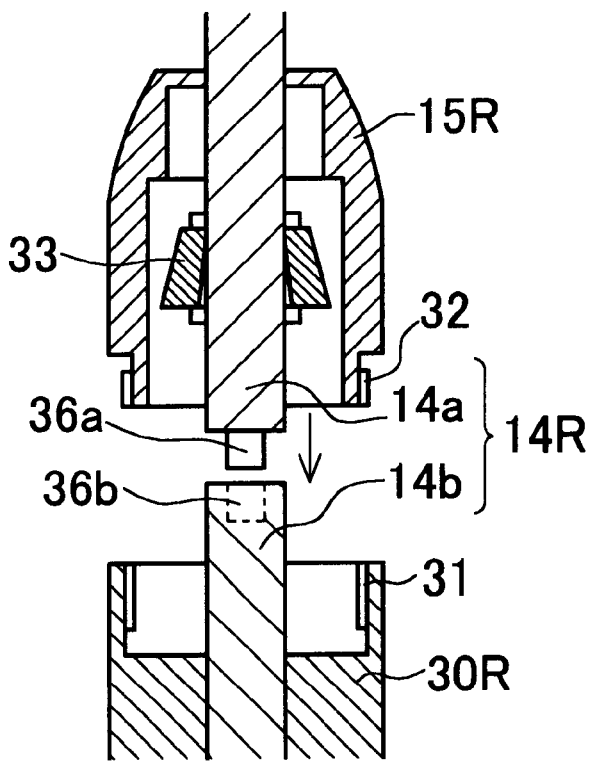
FIG. 6A is a sectional view of another example of a disengaging mechanism of the head support unit of the ophthalmic apparatus according to the present invention.

For example, adaptable is a mechanism of connecting and disconnecting the columns 14R, 14L (the first portions 14a) with respect to the knob retainers 30R, 30L fixed on the base board 5. In this mechanism, as shown in FIG. 6A, the first portion 14a of each of the columns 14R, 14L is provided with a protrusion 36a, while the second portion 14b with an recess 36b which is engageable with the protrusion 36a. With the protrusion 36a engaged with the recess 36b, the first and second column portions 14a and 14b are straight connected, thereby to fix the head support unit 10 upright on the base board 5 by means of the engagement member 33 and the knobs 15R, 15L in the same manner as mentioned above. To the contrary, disconnection of the projection 36a from the recess 36b can cause disassembly of the head support unit 10 from the base board 5.

Figure 6B:
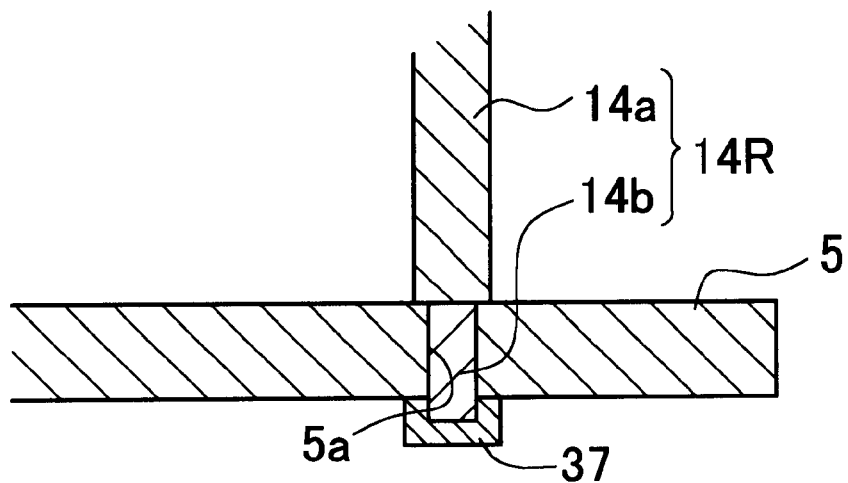
FIG. 6B is a sectional view of another example of a disengaging mechanism of the head support unit of the ophthalmic apparatus according to the present invention.

In another adaptable mechanism, alternatively, the columns 14R, 14L (the first portions 14a) are simply inserted in the base board 5. For example, as shown in FIG. 6B, the second portions 14b of the column 14R (14L) is inserted in amounting hole 5a formed in the board 5 to protrude through the back surface thereof, and a fixing element 37 is attached to the protruded second column portion 14b to secure the column 14R (14L) to the board 5.

In either of the above cases, if cables used for power supply to the fixation lamp 16 are provided in the head support unit 10, they should be arranged so as to be simply removable.

The above embodiment exemplifies a laser treatment apparatus as one of ophthalmic apparatus, but not limited thereto. The present invention can be applied to any ophthalmic apparatus used for observations, measurements, treatments with respect to a patient's eye and provided with a head support unit, such as an eye refractive power measurement apparatus, a slit lamp, and also required transporting.

As described above, according to the present invention, the entire apparatus can be disassembled into a compact state when transported, thus enabling reduction in size of a transportation case. This makes it possible to improve transportability of the apparatus.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:
    a base board;
    a main unit detachably mounted on the base board and provided with at least one of an observation optical system for observing a patient's eye, a measurement optical system for measuring optical characteristics of the patient's eye, and a laser irradiation optical system for applying a treatment laser beam to the patient's eye; and
    a head support unit fixed on the base board, the head support unit being at least foldable to or detachable from the base board.

2. The ophthalmic apparatus according to claim 1, wherein the head support unit includes:
    at least a column provided with a fold portion, and a first and second column portions connected with each other by the fold portion, the second column portion being fixed on the base board; and
    a head support member provided to the first column portion of the column.

3. The ophthalmic apparatus according to claim 2, wherein the head support unit is provided with a first and second fixing members arranged on the first and second column portions respectively, the first and second fixing members being engageable with each other to fixedly hold the first column portion of the column on the base board.

4. The ophthalmic apparatus according to claim 2, wherein the fold portion includes a rotary shaft, and the first column portion is rotated about the rotary shaft in a direction to bring a tip end of the first column portion close to the base board.

5. The ophthalmic apparatus according to claim 1, wherein the head support unit includes:
    at least a column provided with a disengaging portion, and a first and second column portions connected with each other by the disengaging portion, the second column portion being fixed on the base board; and
    a head support member provided to the first column portion of the column.

6. The ophthalmic apparatus according to claim 5, wherein the head support unit is provided with a first and second fixing members arranged on the first and second column portions respectively, the first and second fixing members being engageable with each other to fixedly hold the first column portion of the column on the base board.

7. The ophthalmic apparatus according to claim 1, wherein the head support unit includes:
    at least a column provided with a portion insertable in a through hold formed in the base board;
    a head support member provided on the column; and
    a fixing member engageable with the portion inserted in the through hole and protruded therethrough for fixing the column to the base board.

8. The ophthalmic apparatus according to claim 1 further including a movement system for horizontally moving the main unit on the base board, the system being mounted on the base board and provided with a movable base block, wherein the main unit is detachably mounted on the movable base block.

9. The ophthalmic apparatus according to claim 8, wherein the main unit is provided with a first engagement portion, and the movable base block of the movement system is provided with a second engagement portion engageable with the first engagement portion of the main unit.

10. The ophthalmic apparatus according to claim 8, wherein the movement system includes:
    an axle rotatably inserted in the movable base block, the base block being slidable on the axle;
    gears attached to both ends of the axles; and
    a pair of rails arranged in parallel on the base board and engaged with the gears.

11. The ophthalmic apparatus according to claim 1 further including at least a case for housing together or individually the base board, the main unit, and the head support unit.

12. An ophthalmic apparatus comprising:
    a base board;
    a main unit provided with at least one of an observation optical system for observing a patient's eye, a measurement optical system for measuring optical characteristics of the patient's eye, and a laser irradiation optical system for applying a treatment laser beam to the patient's eye;
    a head support unit fixed on the base board;
    means for enabling mounting and dismounting of the main unit with respect to the base board; and
    means for changing a fixing state of the head support unit with respect to the base board.

13. The ophthalmic apparatus according to claim 12, wherein the changing means includes means for folding the head support unit with respect to the base board.

14. The ophthalmic apparatus according to claim 12, wherein the changing means includes means for disassembling the head support unit from the base board.

15. The ophthalmic apparatus according to claim 12, further including a movement system for horizontally moving the main unit on the base board, the system being mounted on the base board and provided with a movable member, wherein the mounting-dismounting means includes means for mounting and dismounting the main unit with respect to the movable member.

16. The ophthalmic apparatus according to claim 12 further including at least a case for housing together or individually the base board, the main unit dismounted from the base board by means of the mounting-dismounting means, and the head support unit of which a fixing state is changed by the changing means.

* * * * *